(12) United States Patent
Hu et al.

(10) Patent No.: US 11,648,557 B2
(45) Date of Patent: May 16, 2023

(54) METAL ASSISTED CHEMICAL ETCHING FOR FABRICATING HIGH ASPECT RATIO AND STRAIGHT SILICON NANOPILLAR ARRAYS FOR SORTING APPLICATIONS

(71) Applicant: International Business Machines Corporation, Armonk, NY (US)

(72) Inventors: Huan Hu, Yorktown Heights, NY (US); Joshua T. Smith, Croton on Hudson, NY (US); Gustavo A. Stolovitzky, Riverdale, NY (US); Benjamin H. Wunsch, Mt. Kisco, NY (US)

(73) Assignee: International Business Machines Corporation, Armonk, NY (US)

( * ) Notice: Subject to any disclaimer, the term of this patent is extended or adjusted under 35 U.S.C. 154(b) by 806 days.

(21) Appl. No.: 16/581,837

(22) Filed: Sep. 25, 2019

(65) Prior Publication Data
US 2020/0016596 A1 Jan. 16, 2020

Related U.S. Application Data

(62) Division of application No. 15/139,951, filed on Apr. 27, 2016, now Pat. No. 10,507,466.

(51) Int. Cl.
*B01L 3/00* (2006.01)
*H01L 21/3105* (2006.01)
(Continued)

(52) U.S. Cl.
CPC .......... *B01L 3/502753* (2013.01); *B82Y 5/00* (2013.01); *B82Y 15/00* (2013.01);
(Continued)

(58) Field of Classification Search
CPC ....... G01N 15/0255; G01N 2015/0288; G01N 2015/0065; G01N 2015/0053;
(Continued)

(56) References Cited

U.S. PATENT DOCUMENTS 8,278,191 B2 10/2012 Hildreth et al.
8,334,216 B2 12/2012 Lin et al.
(Continued)

OTHER PUBLICATIONS

Hu et al., "Metal Assisted Chemical Etching for Fabricating High Aspect Ratio and Straight Silicon Nanopillar Arrays for Sorting Applications," U.S. Appl. No. 16/581,820, filed Sep. 25, 2019.
(Continued)

*Primary Examiner* — Sang H Nguyen
(74) *Attorney, Agent, or Firm* — Cantor Colburn LLP; Kristofer Haggerty

(57) ABSTRACT

Techniques relate to forming a sorting device. A mesh is formed on top of a substrate. Metal assisted chemical etching is performed to remove substrate material of the substrate at locations of the mesh. Pillars are formed in the substrate by removal of the substrate material. The mesh is removed to leave the pillars in a nanopillar array. The pillars in the nanopillar array are designed with a spacing to sort particles of different sizes such that the particles at or above a predetermined dimension are sorted in a first direction and the particles below the predetermined dimension are sorted in a second direction.

13 Claims, 16 Drawing Sheets

(51) Int. Cl.
  *H01L 21/3213* (2006.01)
  *H01L 29/06* (2006.01)
  *B82Y 5/00* (2011.01)
  *G01N 15/02* (2006.01)
  *B82Y 15/00* (2011.01)
  H01L 21/306 (2006.01)
  G01N 15/00 (2006.01)

(52) U.S. Cl.
  CPC ... *G01N 15/0255* (2013.01); *H01L 21/31055* (2013.01); *H01L 21/31056* (2013.01); *H01L 21/3213* (2013.01); *H01L 29/0676* (2013.01); B01L 2200/0652 (2013.01); B01L 2200/12 (2013.01); B01L 2300/0896 (2013.01); B01L 2400/086 (2013.01); G01N 2015/0053 (2013.01); G01N 2015/0065 (2013.01); G01N 2015/0288 (2013.01); H01L 21/30604 (2013.01)

(58) Field of Classification Search
  CPC .......... H01L 29/0676; H01L 21/31056; H01L 21/3213; H01L 21/31055; H01L 21/30604; B82Y 5/00; B82Y 15/00; B82Y 40/00; B01L 3/502753; B01L 2400/086; B01L 2300/0896; B01L 2200/0652; B01L 2200/12
  See application file for complete search history.

(56) References Cited

U.S. PATENT DOCUMENTS

| | | | |
|---|---|---|---|
| 8,486,843 B2 | 7/2013 | Li et al. | |
| 8,951,430 B2 | 2/2015 | Li et al. | |
| 9,636,675 B2 | 5/2017 | Astier et al. | |
| 2002/0125192 A1 | 9/2002 | Lopez et al. | |
| 2009/0256134 A1 | 10/2009 | Buchine et al. | |
| 2010/0213579 A1* | 8/2010 | Henry | B01J 19/0046 438/719 |
| 2010/0215543 A1* | 8/2010 | Henry | B81C 1/00111 430/296 |
| 2010/0248449 A1 | 9/2010 | Hildreth et al. | |
| 2011/0266521 A1* | 11/2011 | Ferrari | H01L 29/0665 257/14 |
| 2014/0001110 A1* | 1/2014 | Lee | B01L 3/00 977/843 |
| 2014/0167257 A1* | 6/2014 | Mujeeb-U-Rahman | H01L 24/14 257/737 |
| 2014/0256078 A1 | 9/2014 | Jin et al. | |
| 2014/0264937 A1 | 9/2014 | Meitl et al. | |
| 2014/0335411 A1* | 11/2014 | Liu | B81C 1/00539 216/11 |
| 2015/0322589 A1* | 11/2015 | Busnaina | C25D 13/12 219/148 |
| 2015/0367380 A1* | 12/2015 | Kotov | B29C 37/0053 428/206 |
| 2016/0146717 A1* | 5/2016 | Astier | B03B 5/48 438/758 |
| 2017/0120246 A1* | 5/2017 | Hu | G01N 27/44791 |
| 2017/0312747 A1 | 11/2017 | Hu et al. | |

OTHER PUBLICATIONS

Huang, Lotien Richard, et al.; "Continuous Particle Separation Through Deterministic Lateral Displacement"; Science vol. 304; p. 987-990; May 14, 2004.

IBM "List of IBM Patents or Patent Applications Treated as Related; (Appendix P)", Filed Sep. 25, 2019, 2 pages.

Inglis, David W., et al.; "Scaling Deterministic Lateral Displacement Arrays for High Throughput and Dilution-Free Enrichment of Leukocytes"; J. Micromech. Microeng.; vol. 21; p. 1-8; 2011.

Li, Nan, et al.; "On-Chip Continuous Blood Cell Subtype Separation by Deterministic Lateral Displacement" Proceedings of the 2nd IEEE International Conference on Nano/Micro Engineered and Molecular Systems; p. 932-936; Jan. 16-19, 2007.

Li, Xiuling; "Metal Assisted Chemical Etching for High Aspect Ratio Nanostructures: A Review of Characteristics and Applications in Photovoltaics"; Current Opinion in Solid State and Materials Science; vol. 16; p. 71-81; 2012.

Shin, Jae Cheol, et al.; "Experimental Study of Design Parameters in Silicon Micropillar Array Solar Cells Produced by Soft Lithography and Metal-Assisted Chemical Etching"; IEEE Journal of Photovoltaics; vol. 2, No. 2; p. 129-133; Apr. 2012.

\* cited by examiner

SILICON NANOPILLARS FABRICATED BY RIE: NOT STRAIGHT, LIMITED HEIGHT

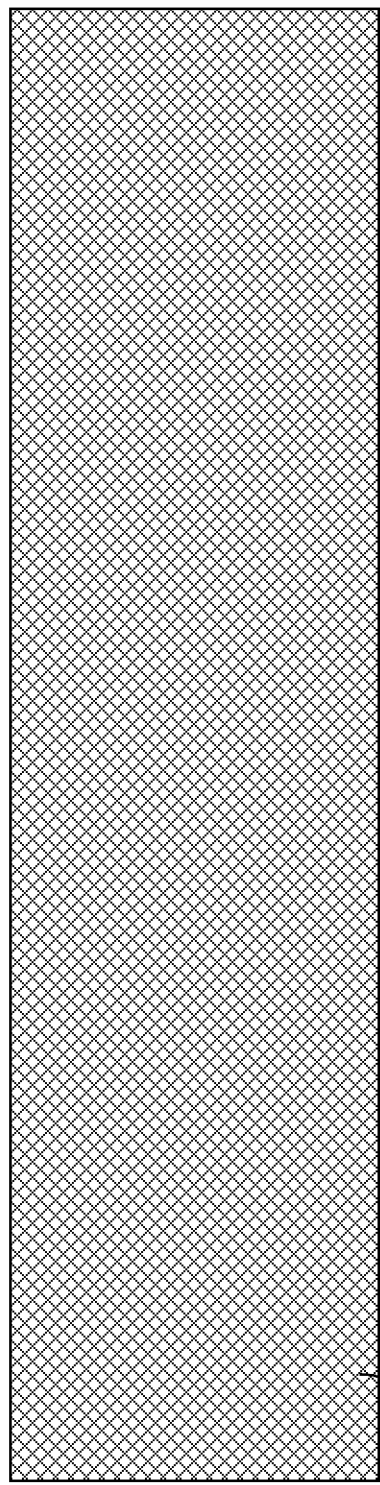
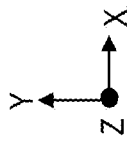
FIG. 2

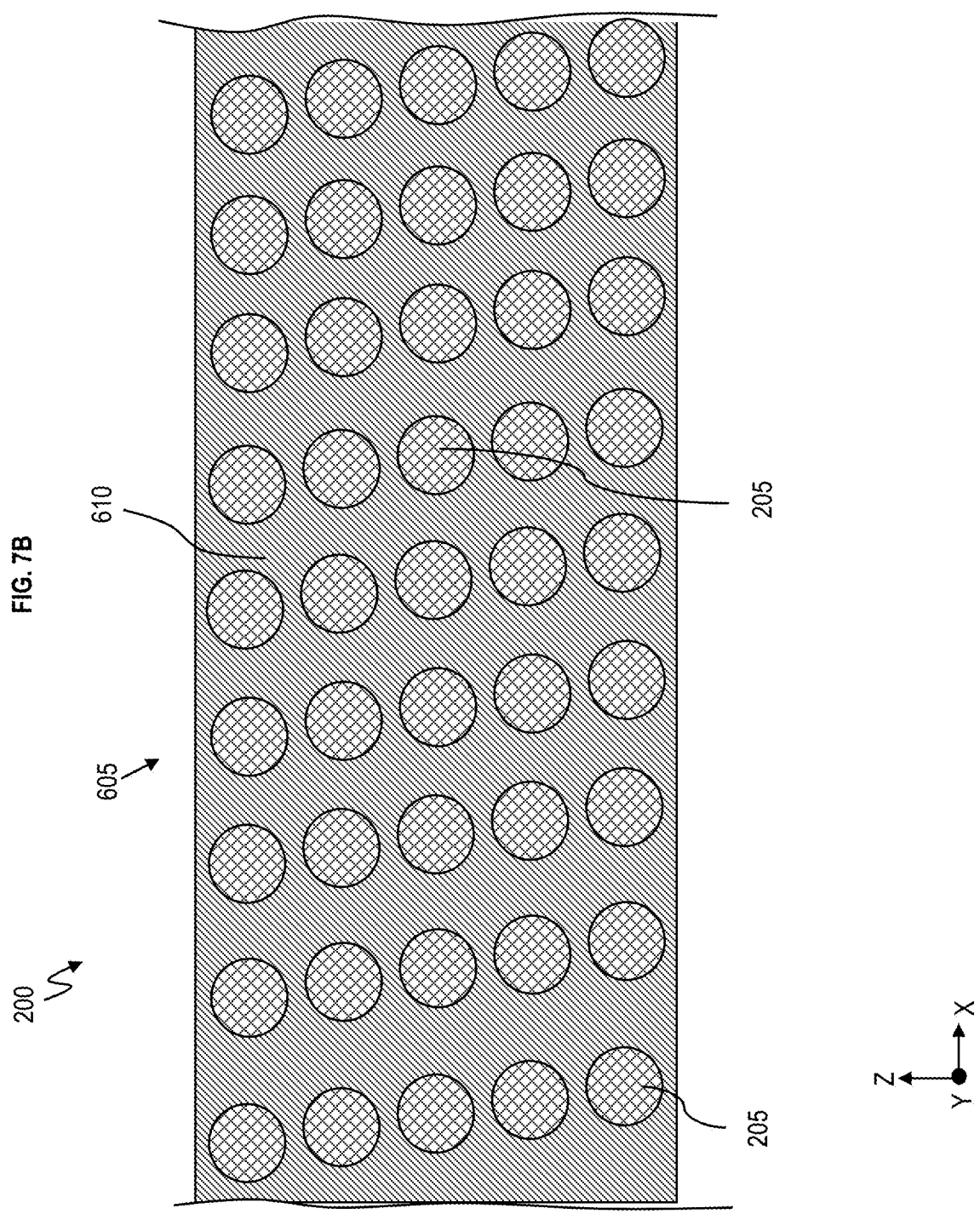

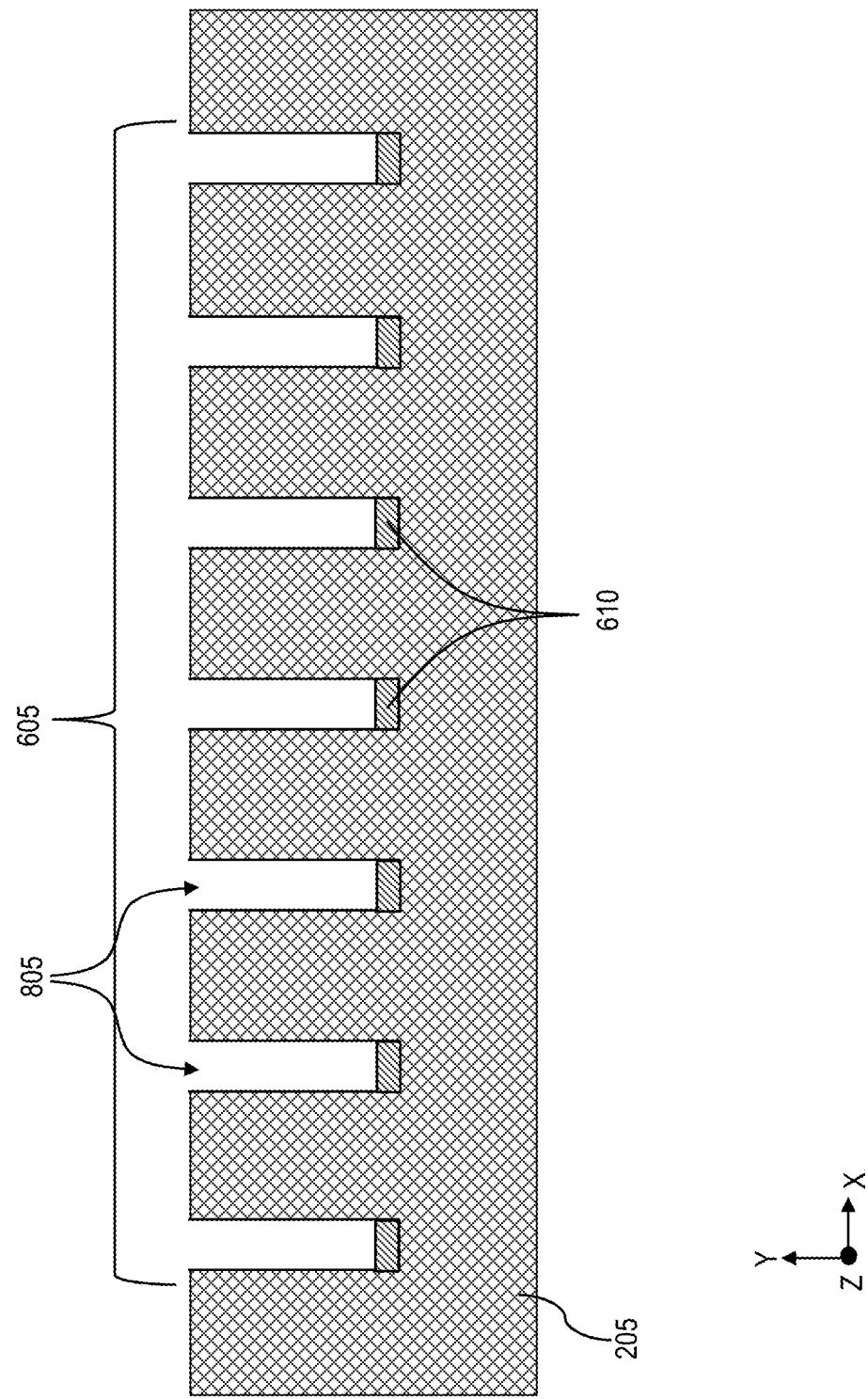

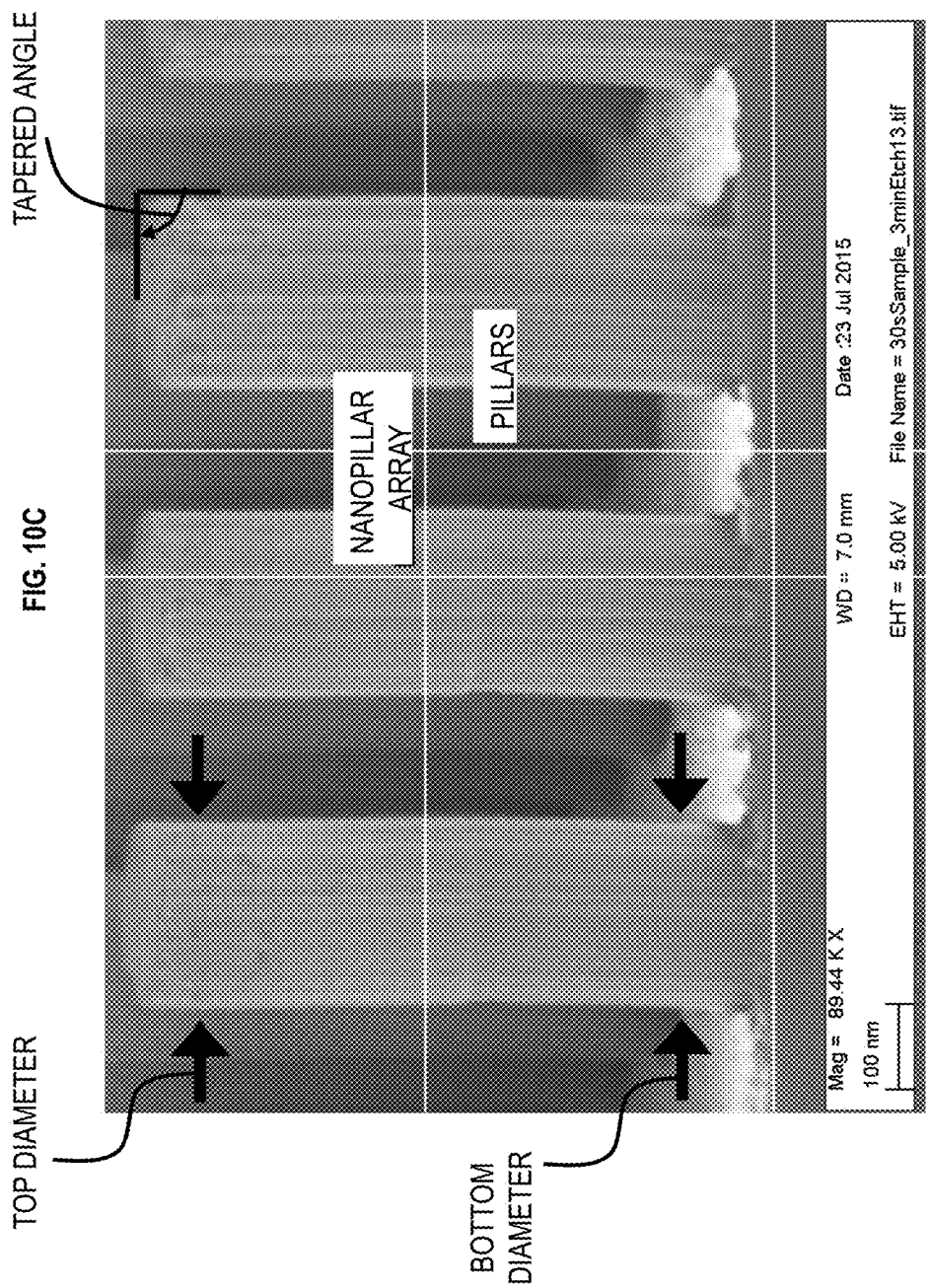

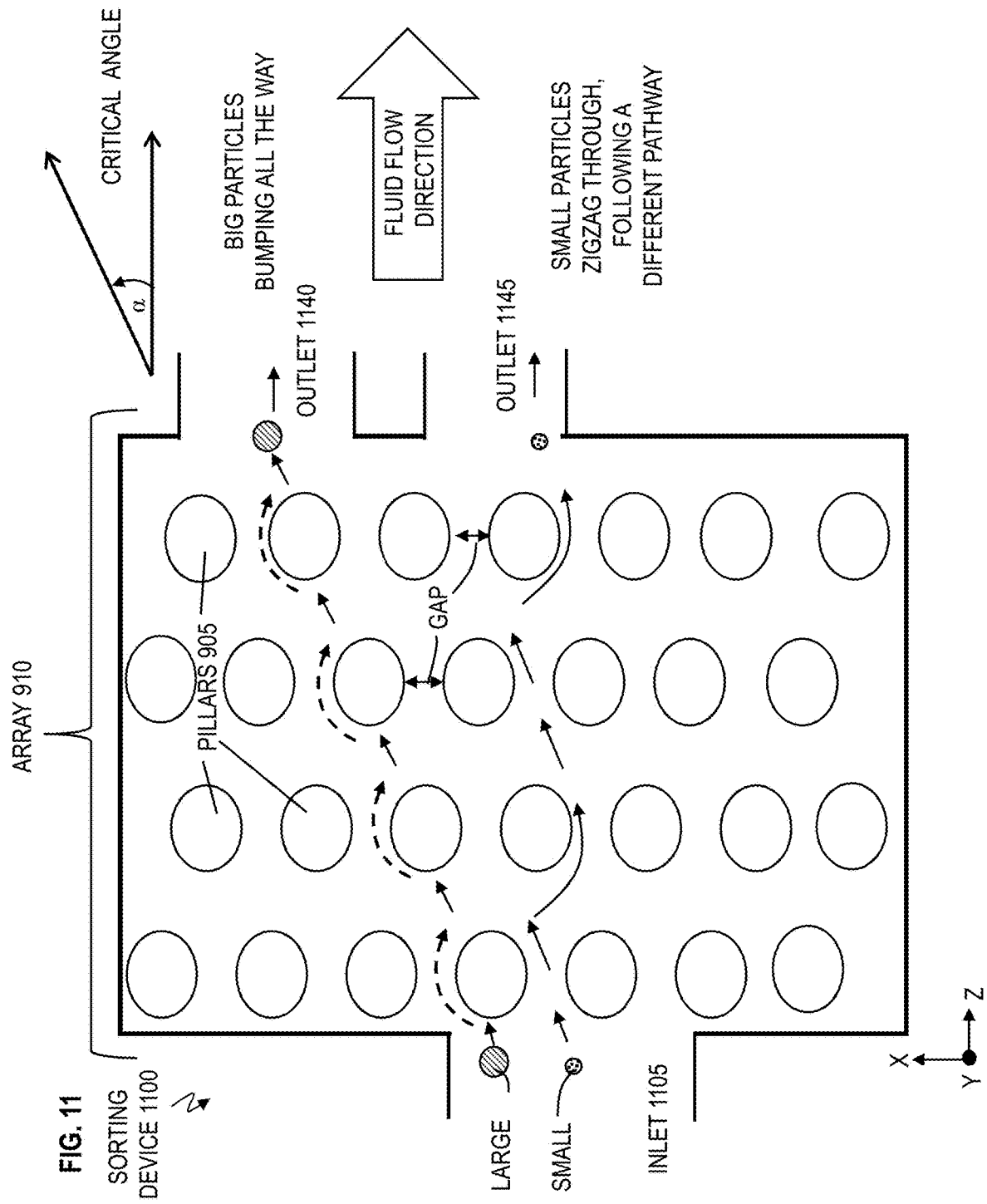

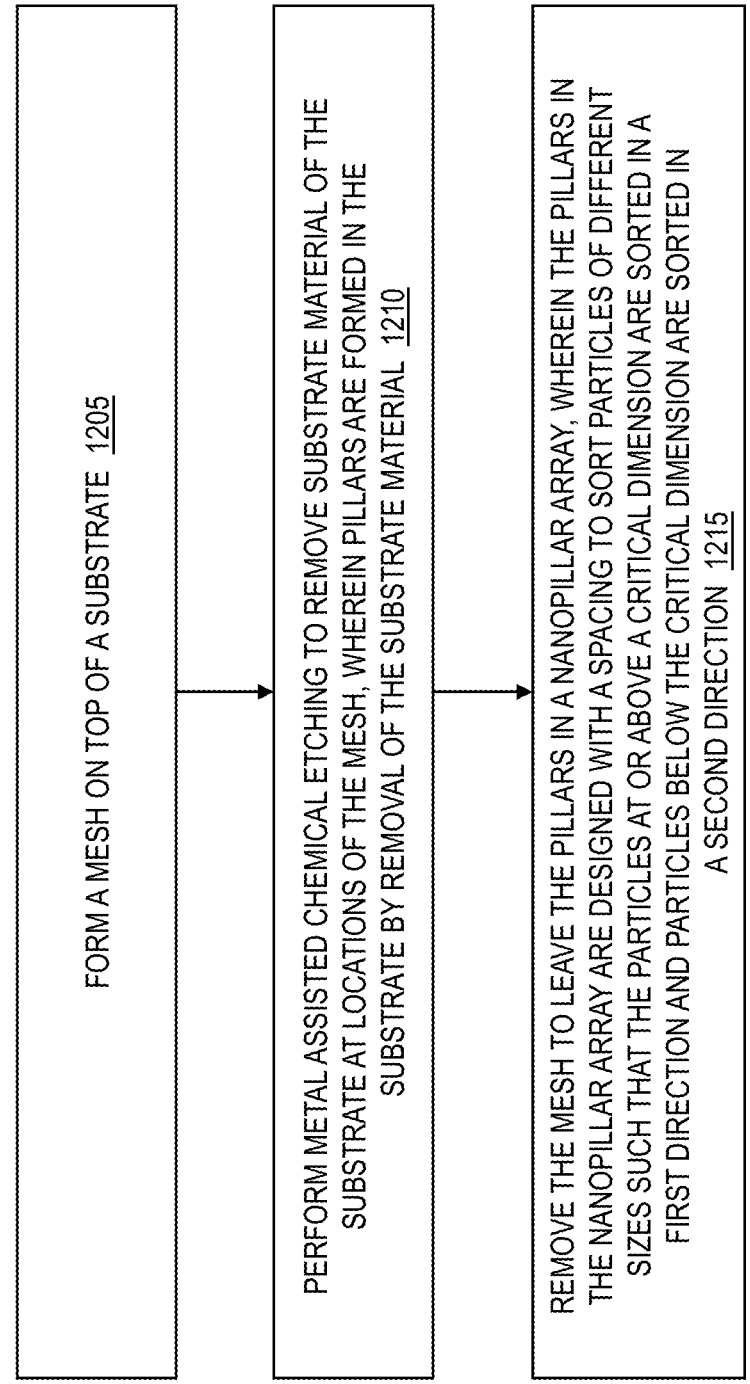

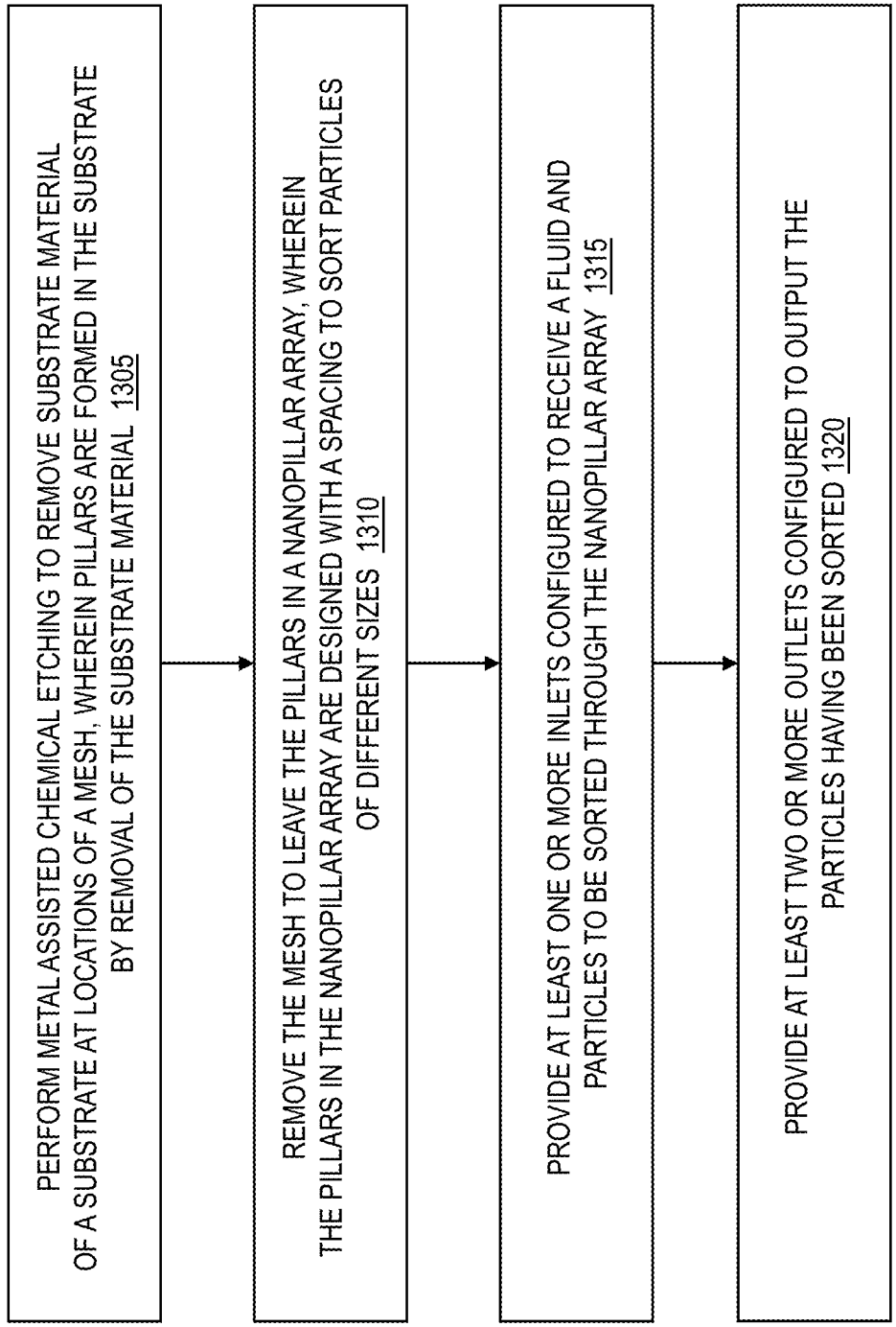

METAL ASSISTED CHEMICAL ETCHING FOR FABRICATING HIGH ASPECT RATIO AND STRAIGHT SILICON NANOPILLAR ARRAYS FOR SORTING APPLICATIONS

DOMESTIC PRIORITY

This application is a divisional of U.S. patent application Ser. No. 15/139,951, filed Apr. 27, 2016, the disclosure of which is incorporated by reference herein in its entirety.

BACKGROUND

The present invention relates to a pillar array structure, and more specifically, to metal-assisted chemical etching for fabricating high aspect ratio and straight silicon nanopillar arrays for sorting applications.

The separation and sorting of biological entities, such as cells, proteins, deoxyribonucleic acid (DNA), ribonucleic acid (RNA), etc., are important to a vast number of biomedical applications including diagnostics, therapeutics, cell biology, and proteomics.

Protein and DNA/RNA separation for analytical purposes is traditionally done by gel electrophoresis, where a protein mix is subjected to a strong electric field (typically 30 volts per centimeter (V/cm)). Proteins or DNA/RNA move through the gel at a rate that depends on their size and surface charge. The gels are prepared from agarose or acrylamide polymers that are known to be toxic. The outcome of the electrophoresis experiment is revealed optically from staining the proteins with dye, or staining the DNA/RNA with ethydium bromide which is extremely carcinogenic. Gels require sufficient quantities of material for the outcome of the electrophoresis to be detectable, but bad cross-linking in the gel matrix often leads to inconclusive results and the complete loss of the samples. If the gel matrix size is not adapted to the sample molecule size or if the electrophoresis is left to run for too long, the sample is also lost.

In comparison with traditional techniques, silicon (Si) nanofabrication technology offers much more precise and accurate control in nano-structural dimensions and positioning of the same, and thus can lead to reliable sorting of particles based on their sizes. To date, Si-based Lab-on-a-Chip approaches using Si pillars arrays have shown promise.

SUMMARY

According to one or more embodiments, a method of forming a sorting device is provided. The method includes forming a mesh on top of a substrate, and performing metal assisted chemical etching to remove substrate material of the substrate at locations of the mesh. Pillars are formed in the substrate by removal of the substrate material. Also, the method includes removing the mesh to leave the pillars in a nanopillar array, where the pillars in the nanopillar array are designed with a spacing to sort particles of different sizes such that the particles at or above a predetermined dimension are sorted in a first direction and the particles below the predetermined dimension are sorted in a second direction.

According to one or more embodiments, a method of forming a sorting device is provided. The method includes performing metal assisted chemical etching to remove substrate material of a substrate at locations of a mesh, where pillars are formed in the substrate by removal of the substrate material, and removing the mesh to leave the pillars in a nanopillar array, where the pillars in the nanopillar array are designed with a spacing to sort particles of different sizes. Also, the method includes providing at least one or more inlets configured to receive a fluid and the particles to be sorted through the nanopillar array, and providing at least two or more outlets configured to output the particles having been sorted.

According to one or more embodiments, a fluidic sorting device is provided. The sorting device includes pillars in a nanopillar array, where the pillars in the nanopillar array are designed with a spacing to sort particles of different sizes, and where the pillars have an aspect ratio greater than 5. Also, the sorting device includes at least one or more inlets configured to receive a fluid and the particles to be sorted through the nanopillar array, and at least two or more outlets configured to output the particles having been sorted.

According to one or more embodiments, a fluidic sorting device is provided. The fluidic sorting device includes pillars in a nanopillar array, where the pillars in the nanopillar array are configured with a spacing to sort particles of different sizes, and where the pillars have an aspect ratio greater than 10. The fluidic sorting device includes at least one or more inlets configured to receive a fluid and the particles to be sorted through the nanopillar array, and at least two or more outlets configured to output the particles having been sorted.

According to one or more embodiments, a method of forming a sorting device is provided. The method includes performing metal assisted chemical etching to remove substrate material of a substrate at locations of a mesh, where pillars are formed in the substrate by removal of the substrate material. The method includes removing the mesh to leave the pillars in a nanopillar array, where the pillars in the nanopillar array are designed with a spacing to sort particles of different sizes. Also, the method includes providing at least one or more inlets configured to receive a fluid and the particles to be sorted through the nanopillar array, and providing at least two or more outlets configured to output the particles having been sorted, where the spacing is configured to sort first particles toward one outlet and sort second particles toward another outlet.

BRIEF DESCRIPTION OF THE DRAWINGS

FIG. 2 is a cross-sectional view of a structure according to one or more embodiments.

FIG. 7B is a top-down view of the structure depicting the mesh layout according to one or more embodiments.

FIG. 8 is a cross-sectional view of the structure depicting formation of pillars in the substrate according to one or more embodiments.

FIG. 10C is a further enlarged view of the scanning electron microscope image of the nanopillar array for the sorting device according to one or more embodiments.

FIG. 11 is a schematic of a sorting device having a nanopillar array according to one or more embodiments.

FIG. 12 is a flow chart of a method of forming a sorting device according to one or more embodiments.

FIG. 13 is a flow chart of a method of forming a sorting device according to one or more embodiments.

DETAILED DESCRIPTION

Figure 1:
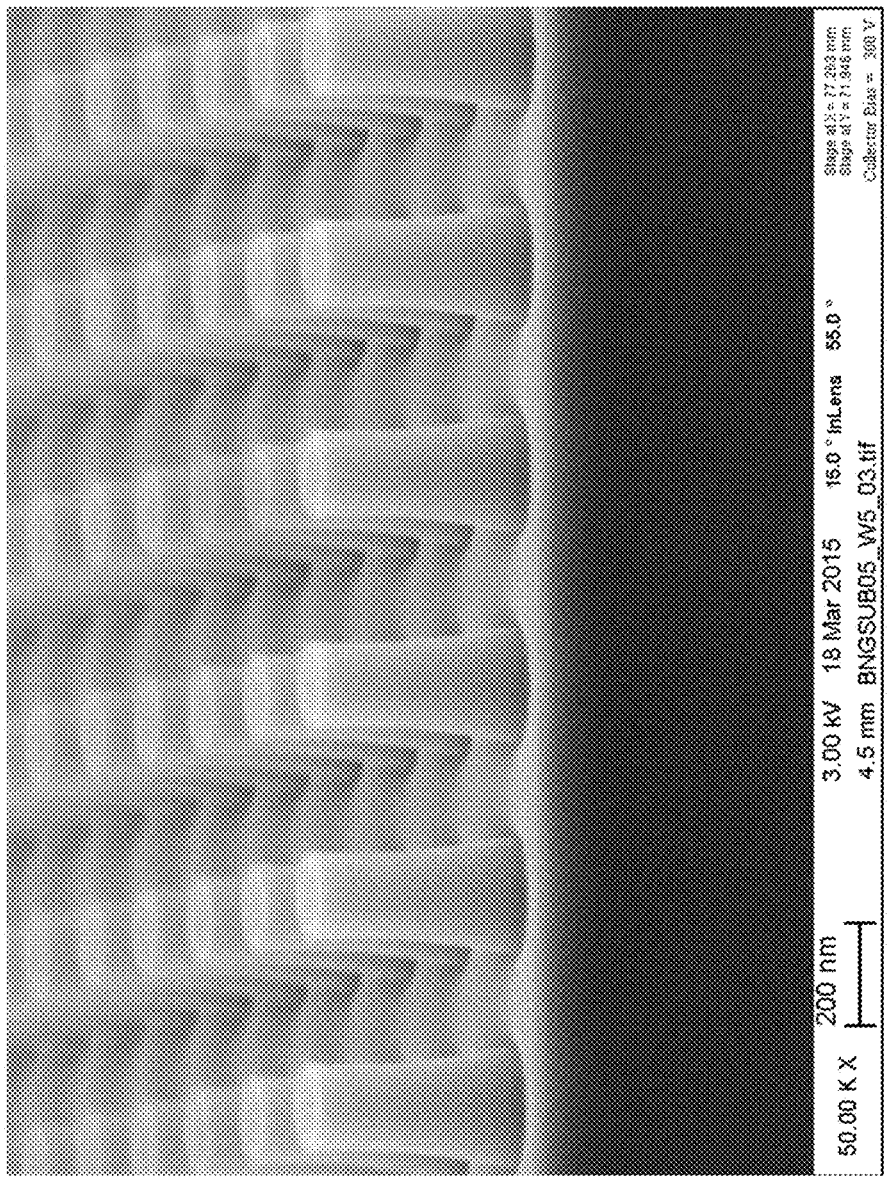
FIG. 1 is a scanning electron microscope image of a nanopillar array formed with reactive ion etching.

Various embodiments are described herein with reference to the related drawings. Alternative embodiments may be devised without departing from the scope of this document. It is noted that various connections and positional relationships (e.g., over, below, adjacent, etc.) are set forth between elements in the following description and in the drawings. These connections and/or positional relationships, unless specified otherwise, may be direct or indirect, and are not intended to be limiting in this respect. Accordingly, a coupling of entities may refer to either a direct or an indirect coupling, and a positional relationship between entities may be a direct or indirect positional relationship. As an example of an indirect positional relationship, references to forming layer "A" over layer "B" include situations in which one or more intermediate layers (e.g., layer "C") is between layer "A" and layer "B" as long as the relevant characteristics and functionalities of layer "A" and layer "B" are not substantially changed by the intermediate layer(s).

Having a high aspect ratio and straight silicon nanopillars is a valuable component in separating biomolecules according to one or more embodiments. However, the current method of fabricating silicon nanopillars, which uses reactive ion etching (RIE), suffers from two disadvantages in the state-of-the-art, and FIG. 1 is a cross-sectional view of a scanning electron microscope (SEM) image of a nanopillar array in the state-of-the-art. First, RIE does not fabricate silicon nanopillars with large depth, and this limits the throughput of the sorting device. Second, the silicon nanopillars fabricated by ME are not straight, resulting into non-uniform gaps between pillars, and the non-uniform gaps deteriorate the efficiency of sorting.

Embodiments demonstrate a new method of fabricating high aspect ratio and straight silicon nanopillars for sorting biomolecules, thereby providing nanopillar arrays with high throughput, thereby being highly efficient sorting devices. Separating biomolecules is recognized as an important step in biomedical analysis and diagnosis. Achieving separation function is indispensable in realizing lab-on-a-chip (LOC). Deterministic lateral displacement (DLD) is an approach discussed for sorting microscale/nanoscale targets based on their sizes using a pillar array. DLD has successfully been used for separating blood cells, tumor cells, leukocytes, etc.

Most of the DLD work uses micrometer scale pillar array for separating micrometer scale targets such as cells. The state-of-the-art has a nanometer scale silicon pillar array, where the silicon nanopillar array was defined by electron beam lithography and etched into silicon by reactive ion etching (RIE). However, RIE is isotropic and can only fabricate limited aspect ratio nanopillars, and the pillar is not straight as shown in FIG. 1. The limited aspect ratio restricts the throughput of the sorting device while the non-straightness of pillars in the array reduces the sorting efficiency.

To solve these two issues, embodiments use metal-assisted chemical etching (MacEtch) to fabricate straight silicon nanopillars in an array with a high aspect ratio. Metal-assisted chemical etching (MacEtch) uses noble metals such as Au, Ag, and Pt as a catalyst to induce local etching of silicon where the noble metal contacts silicon. In order to fabricate a silicon nanopillar array, Au nanoscale meshes are fabricated. As one example, electron beam (e-beam) lithography may be utilized to first pattern poly(Methyl Meth-Acrylate) (PMMA) nanodots on a substrate, evaporation is used to deposit a thin film of Au on top of the PMMA and substrate, and then lift off is performed to remove the PMMA in order to fabricate Au meshes. Additionally, the sample is dipped into an etching solution, which is a mixture of hydrofluoric acid, isopropyl alcohol, and hydrogen peroxide. MacEtch has not been used for fabricating a sorting device having silicon nanopillars.

Embodiments utilize metal assisted chemical etching (MacEtch) for fabricating high aspect ratio and straight vertical silicon nanopillars for sorting applications. MacEtch can fabricate high aspect ratio and straight silicon nanopillars compared with state-of-the-art method of reactive ion etching (RIE). Moreover, in accordance with embodiments, MacEtch can be integrated into the fabrication process since it is a wet etching process employing commonly used chemicals such as hydrofluoric acid, isopropyl alcohol, and hydrogen peroxide.

FIGS. 2-9 illustrate fabrication techniques for building a fluidic sorting device with a nanopillar array according to one or more embodiments. FIG. 2 is a cross-sectional view of a structure 200 according to one or more embodiments. The structure 200 includes a substrate 205. The substrate 205 may be silicon. In one implementation, the substrate 205 may be a silicon wafer. It should be appreciated that other materials may be utilized for the substrate 205.

Figure 3:
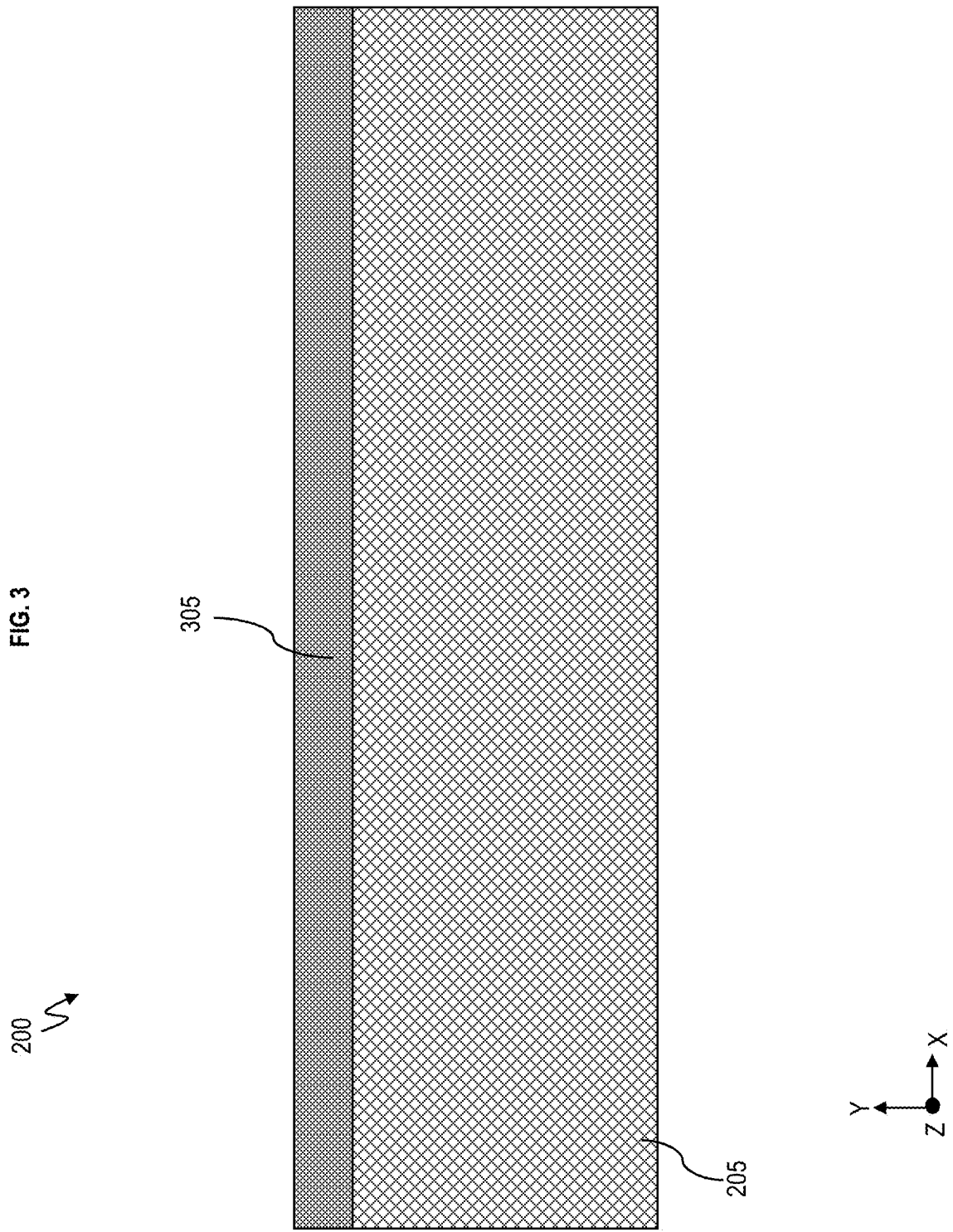
FIG. 3 is a cross-sectional view of the structure depicting deposition of a resist material according to one or more embodiments.

FIG. 3 is a cross-sectional view of the structure 200 depicting deposition of a resist material according to one or more embodiments. A resist 305 is formed on top of the substrate 205. The resist 305 may be a photoresist material designed to be patterned.

Figure 4:
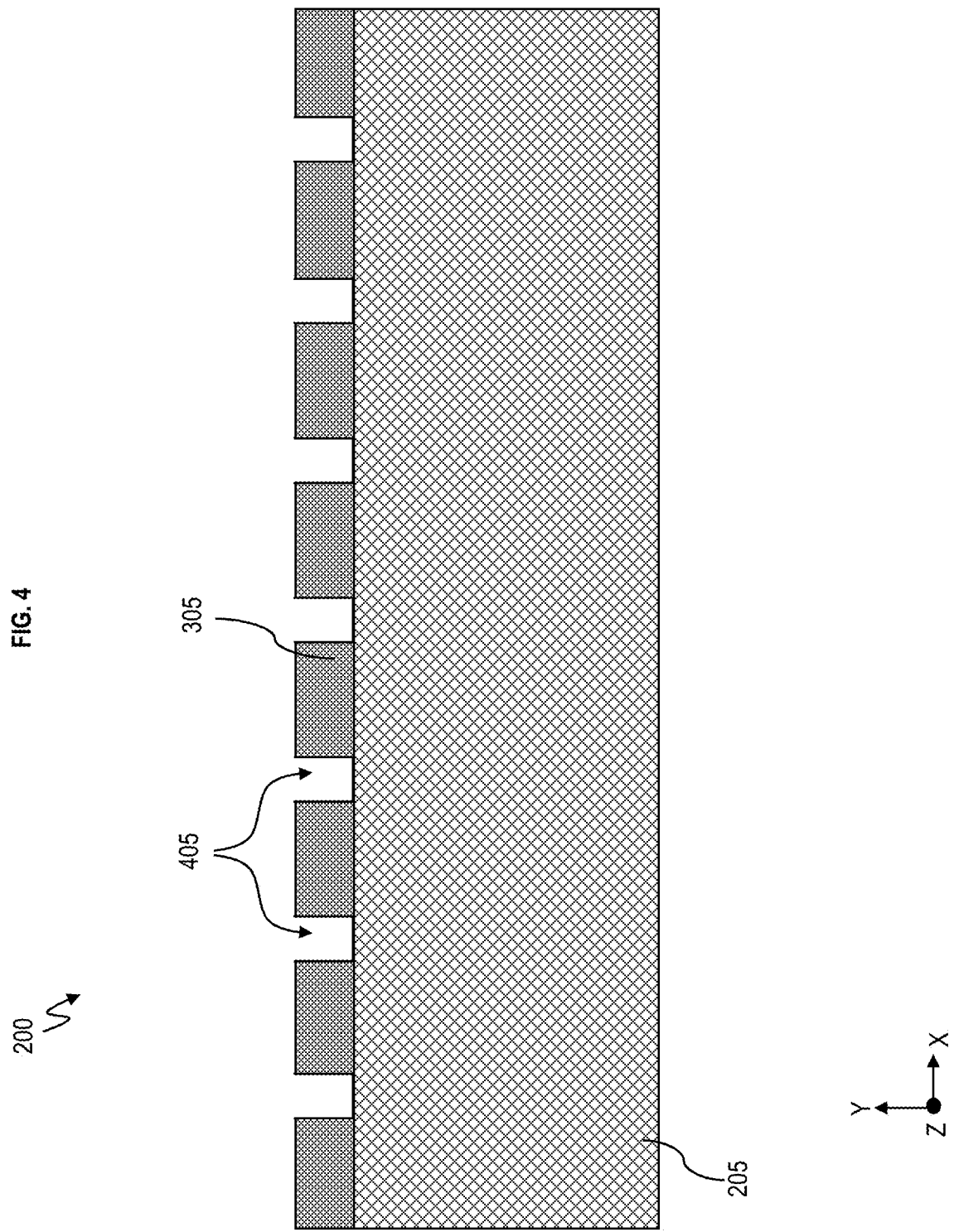
FIG. 4 is a cross-sectional view of the structure depicting patterning of the resist according to one or more embodiments.

FIG. 4 is a cross-sectional view of the structure 200 depicting patterning of the resist 305 according to one or more embodiments. The resist 305 may be etched into a pattern using standard lithography processes. The pattern of the resist 305 has trenches 405. The trenches 405 extend both in a z-axis and an x-axis (not shown in the cross-sectional view) in order to form a nanoscale mesh. Trenches 405 are formed down to the substrate 205 such that the substrate 205 is exposed.

In one implementation, the resist 305 may be patterned using electron beam (e-beam) lithography, and the resist 305 may be PMMA. For example, the patterned resist 305 may be formed into patterned PMMA nanodots using e-beam lithography.

Figure 5:
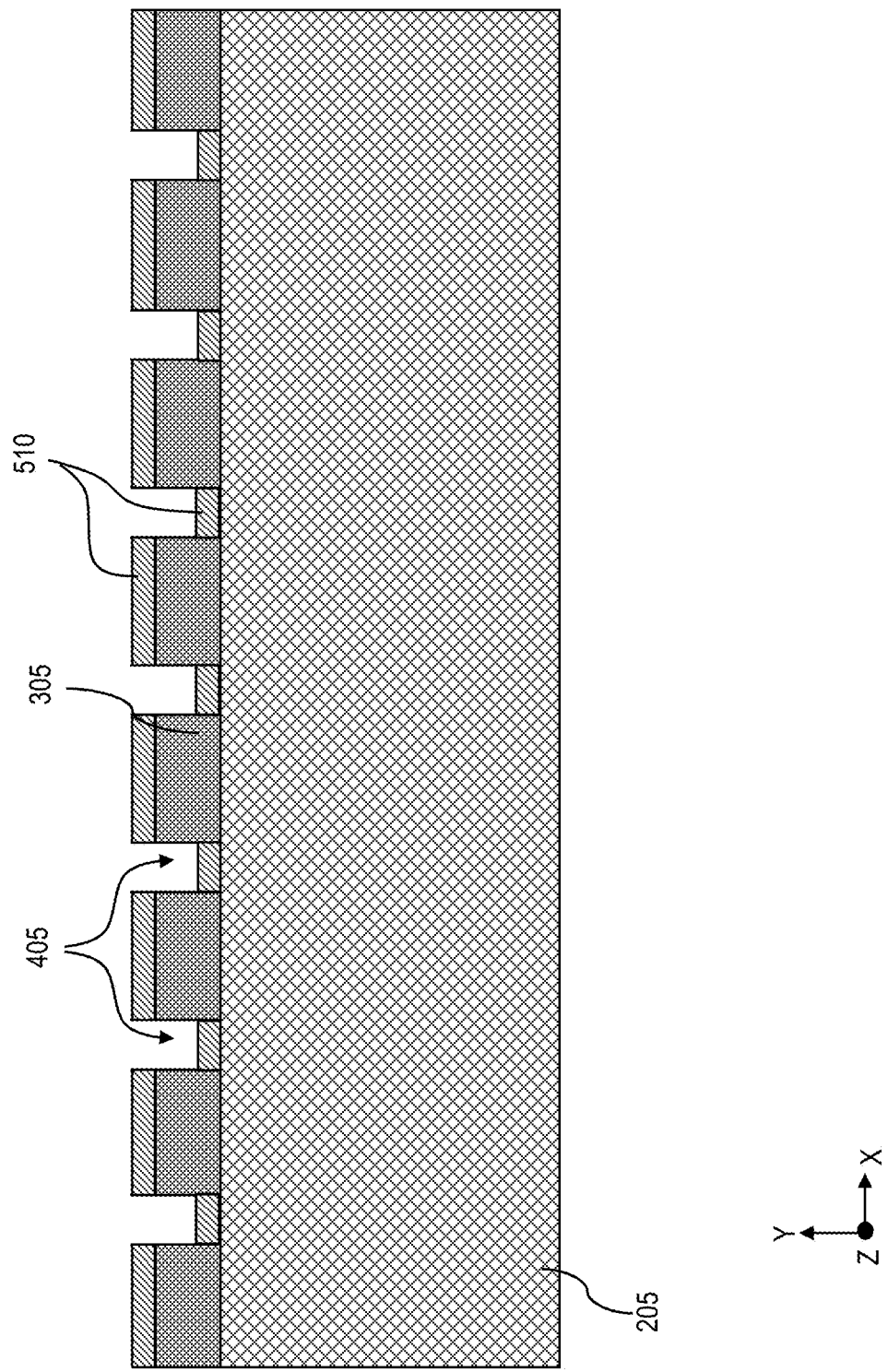
FIG. 5 is a cross-sectional view of the structure depicting deposition of a metal layer according to one or more embodiments.

FIG. 5 is a cross-sectional view of the structure 200 depicting deposition of a metal layer according to one or more embodiments. The patterned resist 305 is utilized to cover certain portions of the substrate 205, while other portions are exposed.

The metal layer 510 may be deposited on top of the patterned resist 305 and the exposed substrate 205 in the trenches 405. Deposition of the metal layer 510 results in portions of the metal layer 510 on top of the resist 305 and portions on top of the substrate 205. The metal layer 510 may be deposited using evaporation as the thin-film deposition technique.

The metal layer 510 may be noble metals. Particularly, the metal layer may be Au, Ag, and/or Pt. In one implementation, Au may be better for etching a silicon substrate.

Figure 6:
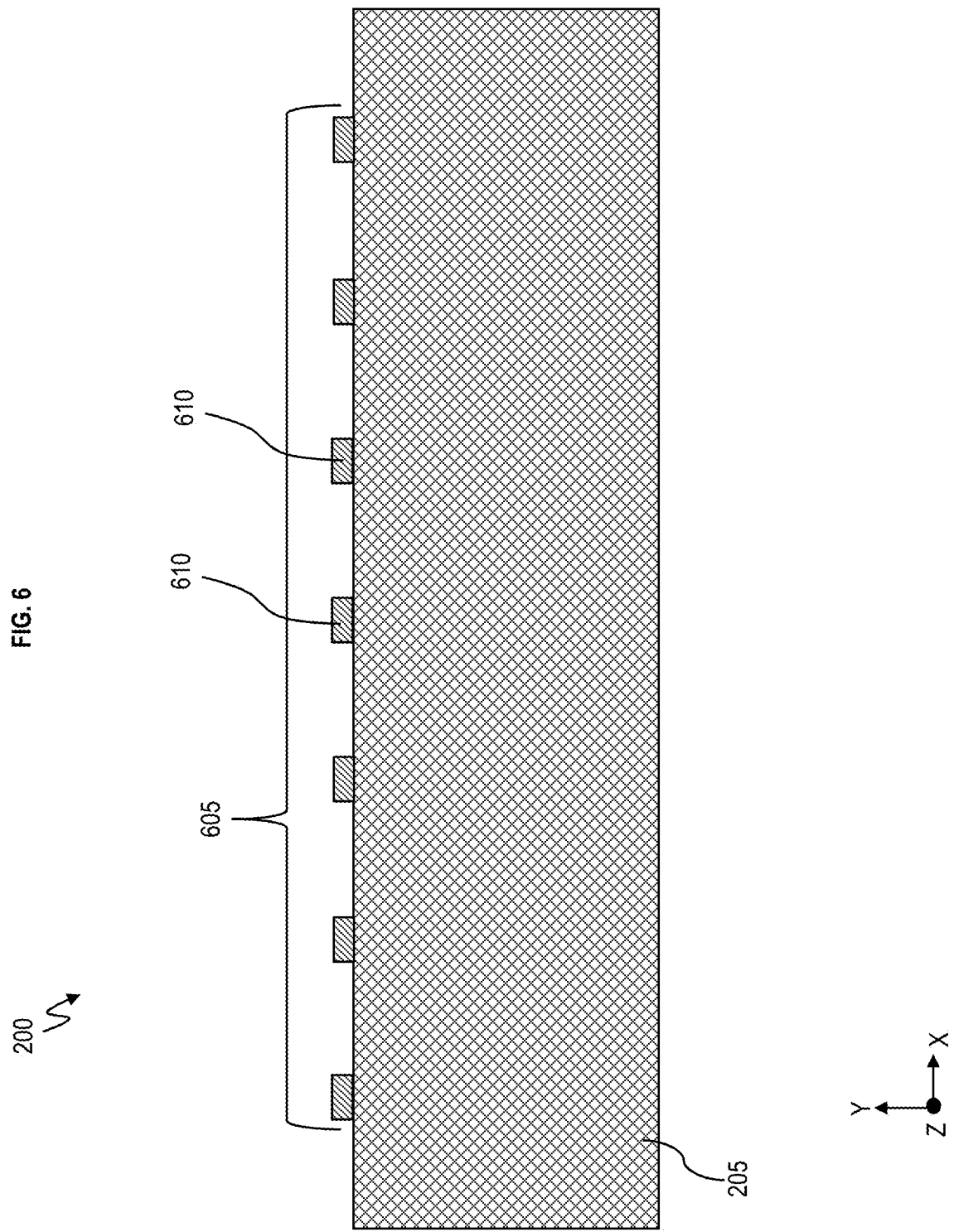
FIG. 6 is a cross-sectional view of the structure depicting formation of a nanoscale mesh according to one or more embodiments.

FIG. 6 is a cross-sectional view of the structure 200 depicting formation of a nanoscale mesh according to one or more embodiments. To form the mesh 605 of the metal layer 510, the patterned resist 305 is lifted off, thereby removing the portions of the metal layer 510 on top of the resist 305. The resist 305 may be lifted off using, for example, acetone.

After removal of the resist 305, the metal layer 510 that was previously on the exposed substrate 205 in the trenches 405 still remains as metal lines/strips 610. The mesh 605 is a network of the connected metal lines 610 running in both the x-axis and z-axis. The mesh 605 may be similar to a web or a net in that it has many attached strands of metal lines 610. The mesh 605 is directly on top of the substrate 205.

It is appreciated that other techniques may be utilized to deposit the metal layer 510 and form the mesh 605 of metal lines 610. In one case, the metal layer 510 may be deposited directly on top of the substrate 205 without using the resist 305. The metal layer 510 may be etched using lithography into the mesh 605 of metal lines 610. In another case, once the metal layer 510 is deposited on top of the substrate 205, a resist may be formed on top of the metal layer 510 and patterned into a pattern such that the desired metal lines 610 are covered by the resist. Accordingly, the exposed portions of the metal layer 510 are removed along with the resist, such that the mesh 605 remains.

Figure 7A:
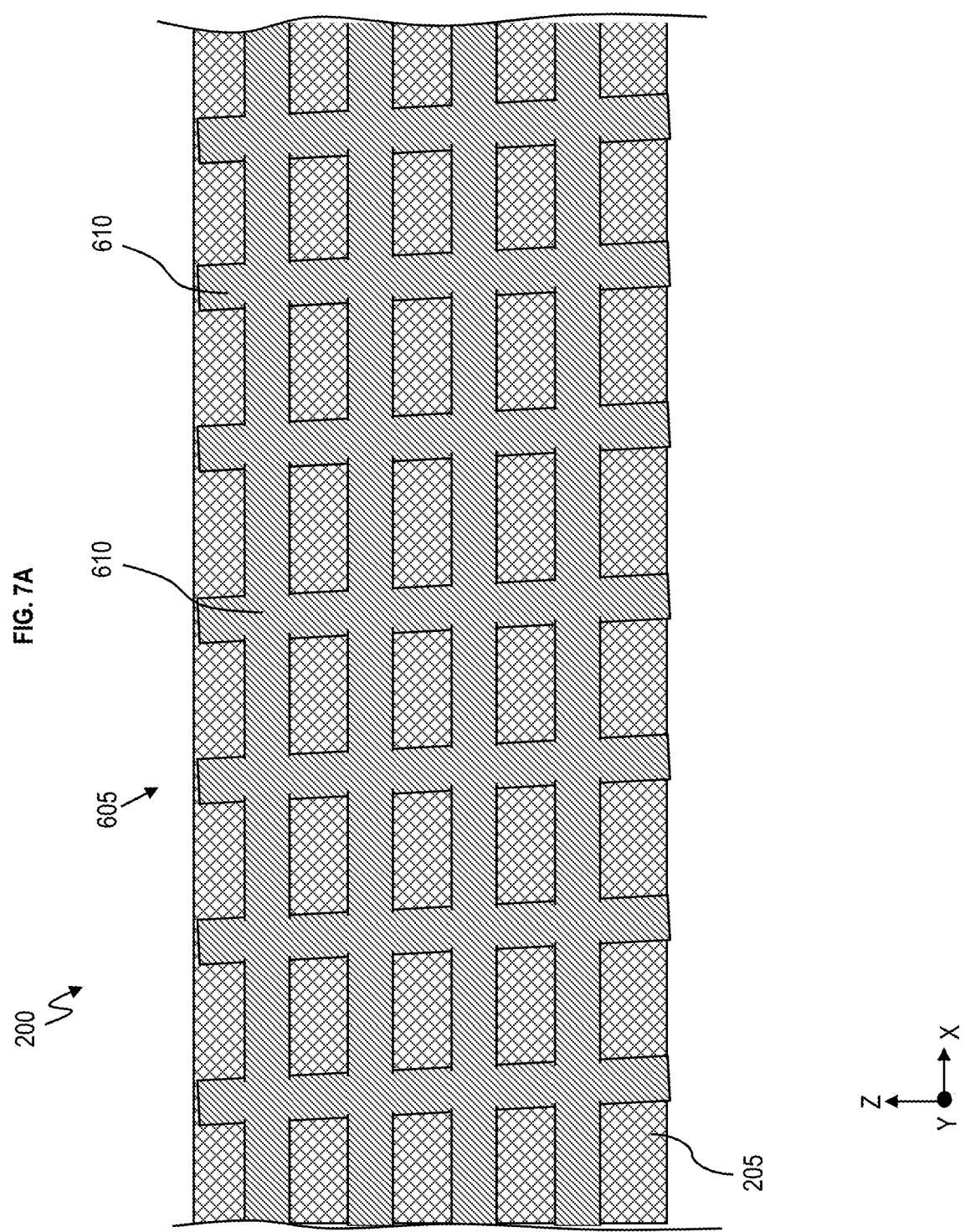
FIG. 7A is a top-down view of the structure depicting the mesh layout according to one or more embodiments.

FIG. 7A is a top-down view of the structure 200 depicting the mesh 605 according to one or more embodiments. As can be seen, the mesh 605 includes connected metal lines 610. In between the connected metal lines 610 are exposed portions of the substrate 205. These exposed portions of the substrate 205 are the locations for which pillars are to be formed and also correspond to areas where the patterned resist 305 has been lifted off.

FIG. 7B is a top-down view of the structure 200 depicting the mesh 605 according to one or more embodiments. FIG. 7B also illustrates connected metal lines 610 that form the mesh 605. In FIG. 7B, exposed portions of the substrate 205 may be more circular as compared to FIG. 7A because of the nanodots of exposed substrate 205 are circular. As noted above, these exposed portions of the substrate 205 are the locations for which pillars are to be formed and also correspond to areas where the patterned resist 305 has been removed.

FIG. 8 is a cross-sectional view of the structure 200 depicting formation of pillars in the substrate according to one or more embodiments. The substrate 205 may be etched according to the pattern of the mesh 605. Trenches 805 are formed in the substrate 205 following the pattern of the mesh 605. Accordingly, the trenches 805 mirror the connected network of the metal lines 610.

The trenches 805 are etched into the substrate 205 using metal assisted chemical etching (MacEtch). In one implementation, the MacEtch may use a mixture of hydrofluoric (HF) acid, isopropyl alcohol, and hydrogen peroxide as an etchant to etch silicon.

Metal assisted chemical etching is also abbreviated as MaCE or MCE. MacEtch is a wet but directional etch technique. MacEtch uses noble metals to induce local oxidation and reduction reactions under open circuit. Metal such as Au, Pt and Ag, deposited on the surface of a semiconductor (e.g., Si) serves as a local cathode to catalyze the reduction of oxidants (e.g., $H_2O_2$) producing holes (h+). The holes (h+) are then injected into the valence band of the semiconductor to oxidize and form the ionic form that is soluble in an acidic solution (e.g., HF). This results in the removal of semiconductor materials without net consumption of the metal. Under controlled etching conditions, MacEtch reactions occur only at the interface between metal and the semiconductor. As a result, metal descends into the semiconductor as the semiconductor is being etched right underneath, acting as a negative resist etch mask. When the catalyst metal is patterned in any shape and dimension, the pattern can be engraved into the semiconductor to produce microstructures and nanostructures including arrays of pillars.

Figure 9:
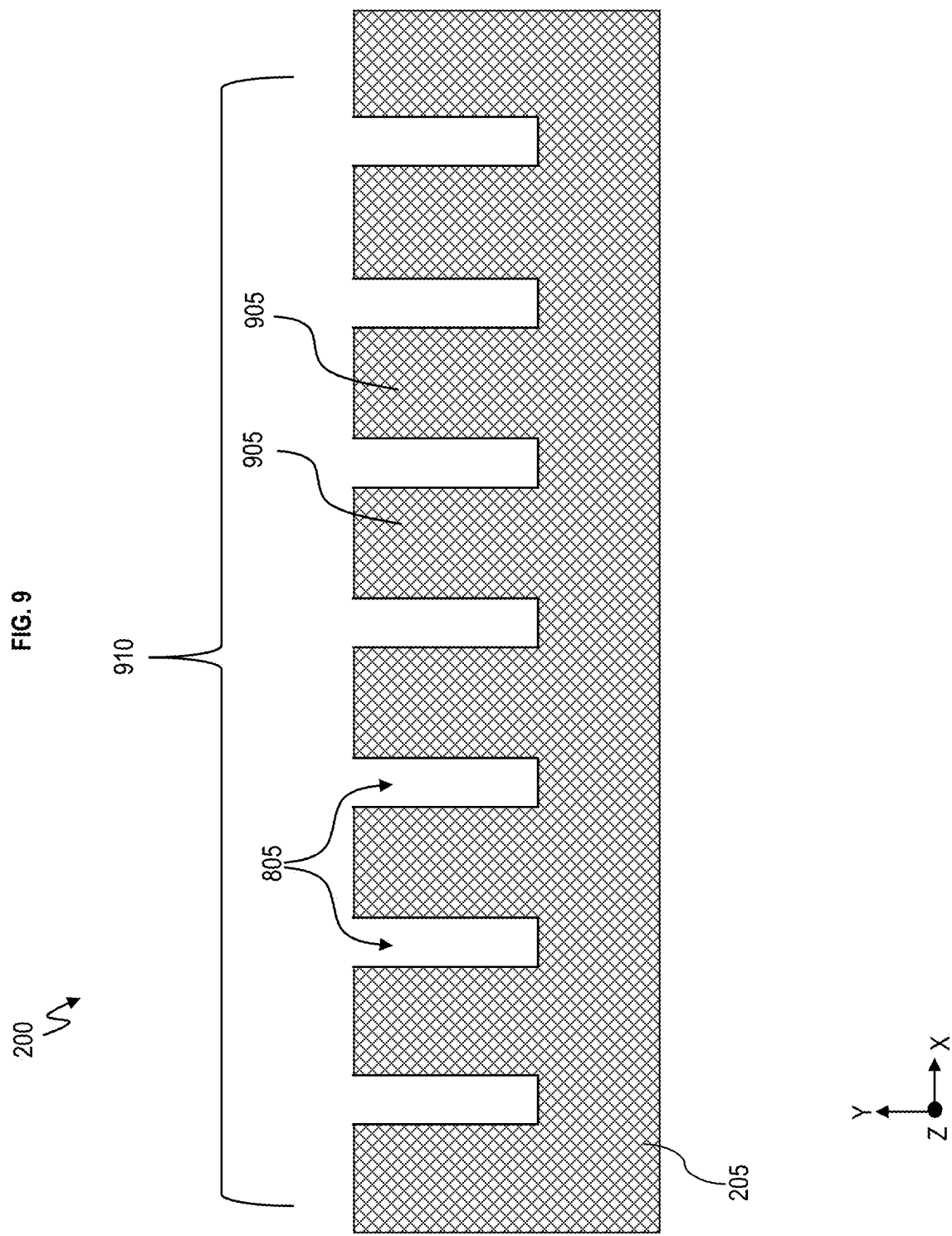
FIG. 9 is a cross-sectional view of the structure depicting pillars of a nanopillar array according to one or more embodiments.

FIG. 9 is a cross-sectional view of the structure 200 depicting pillars 905 in a nanopillar array 910 of a sorting device according to one or more embodiments. The metal lines 610 are removed from the trenches 805 resulting in pillars 905 of the nanopillar array 910. It should be appreciated that the nanopillar array 910 may have numerous rows and columns of pillars 905. There may be tens, hundreds, or thousands of pillars 905. Each of the pillars 905 are separated from one another by trenches 805 running in both the x-axis and y-axis. The spacing is designed to separate particles of different sizes as discussed further herein.

Figure 10A:
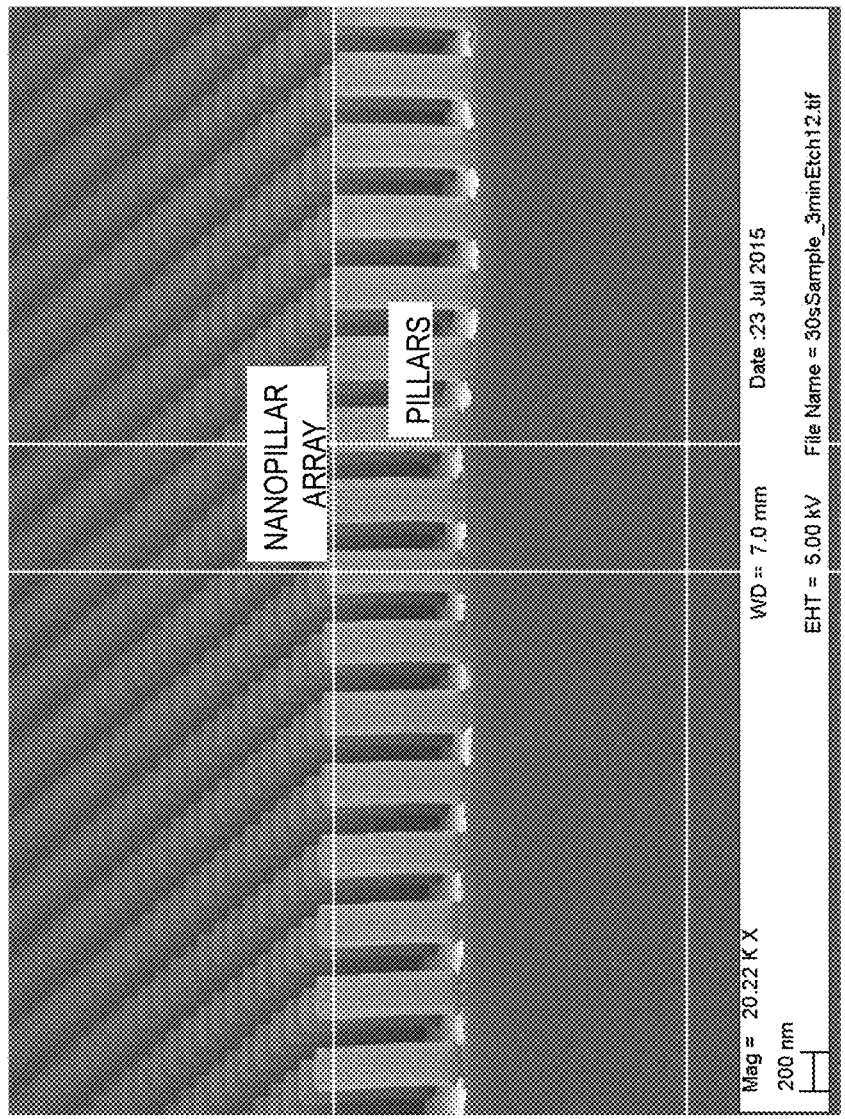
FIG. 10A is a scanning electron microscope image of a nanopillar array for a sorting device according to one or more embodiments.
Figure 10B:
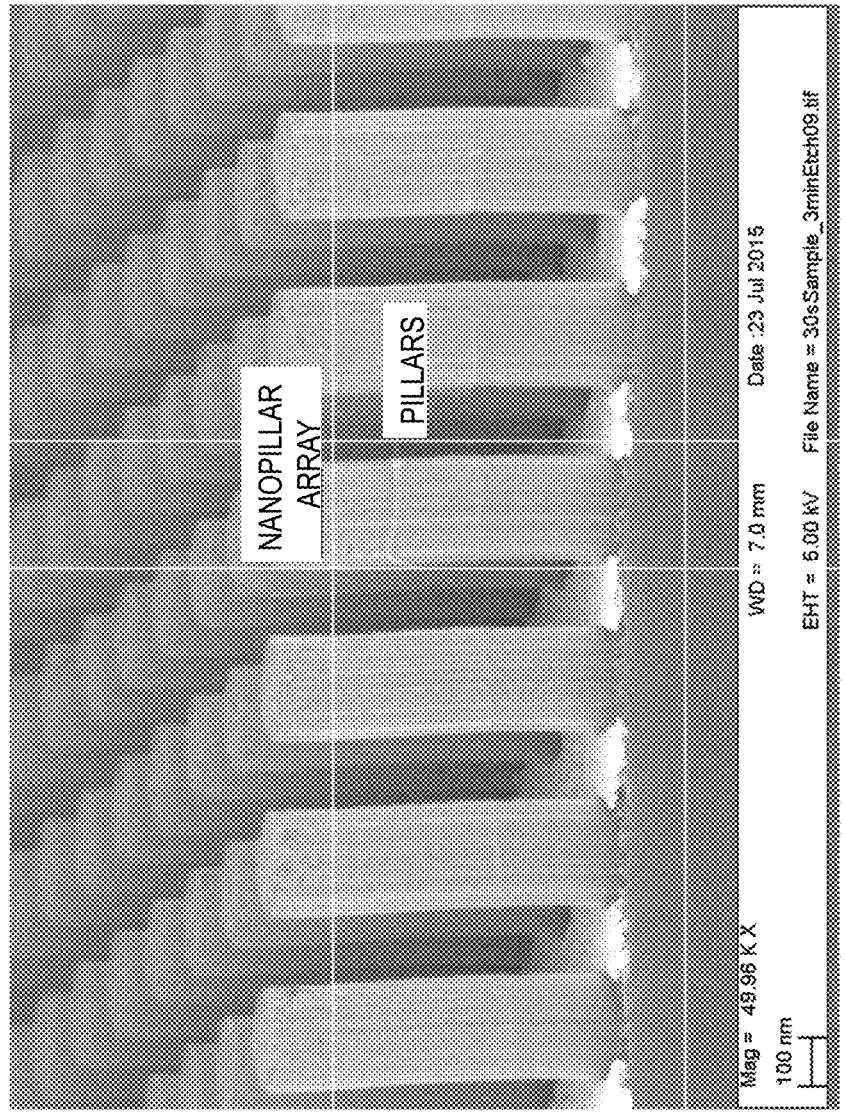
FIG. 10B is an enlarged view of the scanning electron microscope image of the nanopillar array for the sorting device according to one or more embodiments.

FIG. 10A is a scanning microscope image of pillars in a nanopillar array of a sorting device according to one or more embodiments. FIG. 10B is an enlarged view of the pillars in the nanopillar array of the sorting device according to one or more embodiments. FIG. 10C is a further enlarged view of the pillars in the nanopillar array of the sorting device according to one or more embodiments. FIGS. 10A, 10B, 10C are silicon nanopillars in the sorting array formed using MacEtch as discussed herein. It should be appreciated that no oxide or other material needs to be formed on and around the pillars to make the pillars vertically straight.

In FIGS. 10A, 10B, 10C, the pillars (e.g., pillars 905) are illustrated with a top diameter of about 224 nm, a bottom diameter of about 226 nm, a height of about 728 nm, and a tapered angle of about 90°. Also, the pillars may have an aspect ratio of about 3.25, where the aspect ratio is height/diameter (e.g., 728/224=3.25).

The pillars 905 in the nanopillar array 910 may have an aspect ratio of about 5 or greater. In one implementation, the pillars 905 in the nanopillar array 910 may have an aspect ratio up to or through about 100. In another implementation, the pillars 905 in the nanopillar array 910 may have an aspect ratio up to or through about 200. In one particular implementation, the pillars 905 may have an aspect ratio of about 10-100. The fluidic sorting device (e.g., sorting device 1100) discussed herein is designed to have such high aspect ratios because the pillars 905 are straight (in the vertical direction in the y-axis), the pillars 905 have substantially a uniform diameter/width from top to bottom, and the pillars 905 have substantially uniform spacing between one another. Having vertically straight pillars 905 provides a greater throughput which means that more particles can simultaneously be sorted. Having a uniform diameter and uniform spacing provides consistent sorting (i.e., fewer errors) such that particles of different sizes are sorted in the respective directions through the nanopillar array 910.

In contrast, nanopillar arrays in sorting devices of the state-of-the-art have pillars that are bowed in as shown in FIG. 1. Accordingly, the silicon material of the pillars 905 do not form a uniform diameter/width from top to bottom, and do not have uniform spacing between the pillars. Therefore, the sorting devices in the state-of-the-art have a smaller throughput thereby limiting the particles can simultaneously be sorted because of the non-uniform spacing between pillars. Additionally, pillars in sorting device of the state-of-the-art have a low aspect ratio which is normally 1 and is less than 3.

FIG. 11 is a schematic of a sorting device 1100 having the nanopillar array 910 according to one or more embodiments. The sorting device 1100 is a fluidic device designed to pass fluid. The fluidic sorting device 1100 separates particles based on a predetermined critical dimension that the nanopillar array 910 is designed to accommodate for separating particles. The predetermined critical dimension is based on the gap between the pillars 905, where the gap is the uniform spacing between the pillars 905. The particles may be biological entities, such as cells, proteins, deoxyribonucleic acid (DNA), ribonucleic acid (RNA), etc.

The sorting device 1100 has an inlet 1105 to receive fluid containing the different sized particles (i.e., biological entities) to be sorted. For example, there may be large/larger particles that need to be separated from small/smaller particles. Although one inlet 1105 is shown, the sorting device 1100 may include one inlet for inputting the particles and another inlet for inputting the fluid.

The inlet 1105 may be an opening or hole in the walls around the nanopillar array 910 or may span the width of the nanopillar array 910 through which fluid (e.g., water, electrolyte solutions, organic solvents, etc.) and particles (e.g., biological entities) can flow. Particles having a size greater than the predetermined critical dimension are bumped (i.e., bumped mode) through the nanopillar array 910 in the direction of the predetermined critical angle α to be collected at outlet 1140, and the particles smaller than the critical dimension are collected at outlet 1145.

The predetermined critical dimension is the size (e.g., diameter) of a round shaped particle and/or persistence length of a chain structure, such as DNA, that is too large to zigzag through the nanopillar array 910. Particles, having a size smaller than the critical dimension, zigzag (i.e., zigzag mode) through the nanopillar array 910 in the direction of fluid flow, and the smaller particles are collected at the outlet 1145. The particles having the size smaller than the critical dimension follow the direction of the fluid flow, and are sorted through the outlet 1145.

The outlets 1140 and 1145 may be openings through which the sorted particles can flow such that the particles are collected in bins after sorting. The inlet 1105 and outlets 1140 and 1145 may be openings in the walls of the substrate material of the substrate 205 that surrounds the pillars 905. The sorting device 1100 is a fluidic device designed to hold fluid and allow the fluid to flow in a fluid flow direction, such that the both fluid and the particles to be separated flow in the fluid flow direction toward outlets 1140 and 1145. In one implementation, the sorting device 1100 may be encased or partially encased in a plastic-like housing. The housing may contain one or more openings to receive the fluid and particles at one side. Also, the housing contains openings to output the fluid and separated particles at an opposite side.

FIG. 12 is a flow chart of a method 1200 of forming a sorting device 1100 according to one or more embodiments. Reference can be made to FIGS. 2-11.

At block 1205, a mesh 605 is formed on top of a substrate 205.

At block 1210, metal assisted chemical etching is performed to remove substrate material of the substrate 205 at locations of the mesh 605, where pillars 905 are formed in the substrate 205 by removal of the substrate material.

At block 1215, the mesh 605 is removed to leave the pillars 905 in the nanopillar array 910, where the pillars 905 in the nanopillar array 910 are designed with a spacing (i.e., gap) to sort particles of different sizes such that the particles at or above a critical dimension are sorted in a first direction (e.g., to outlet 1140) and particles below the critical dimension are sorted in a second direction (e.g., to outlet 1145).

The pillars 905 are spaced from one another to thereby form the nanopillar array 910. The mesh 605 is a metal. The metal of the mesh 605 is a selection of noble metals. The metal of the mesh 605 includes at least one of Au, Ag, and Pt.

The substrate 205 is silicon. The pillars 905 are straight in a vertical direction. The substrate material forming a bottom, a middle, and a top of the pillars 905 has substantially the same width/diameter. The substrate material forming the pillars 905 is not bowed inward at a middle of the pillars. The spacing (i.e., gap) between a bottom, a middle, and a top of the pillars is substantially the same.

The pillars 905 have an aspect ratio greater than 5. The pillars 905 have an aspect ratio of greater than 10. The pillars 905 have an aspect ratio of about 10 to 100. The pillars 905 have an aspect ratio up to 200.

FIG. 13 is a flow chart of a method 1300 of forming a sorting device 1100 according to one or more embodiments. Reference can be made to FIGS. 2-12.

At block 1305, metal assisted chemical etching is performed to remove substrate material of a substrate 205 at locations of a mesh 605, where pillars 905 are formed in the substrate 205 by removal of the substrate material.

At block 1310, the mesh 605 is removed to leave the pillars 905 in the nanopillar array 910, where the pillars in the nanopillar array are designed with a spacing to sort particles of different sizes.

At block 1315, at least one or more inlets 1105 are configured to receive a fluid and particles to be sorted through the nanopillar array 910.

At block 1320, at least two or more outlets 1140, 1145 are configured to output the particles having been sorted.

The pillars 905 may have an aspect ratio up to 100 or have an aspect ratio up to 200.

The spacing is designed to sort first particles (e.g., large particles) toward one outlet (e.g., such as outlet 1140) and sort second particles (e.g., small particles below a critical dimension) toward another outlet (e.g., outlet 1145).

Technical effects and benefits include improved semiconductor devices, including, for example, improved fluidic sorting devices. The sorting device includes a nanopillar array with straight pillars having a high aspect ratio. The high aspect ratio allows greater throughput of particles and greater sorting capability. The straight pillars in the nanopillar array provide consistent sorting because the gap (i.e., spacing) is consistent from top to bottom between neighboring pillars.

It should be appreciated that the design for semiconductor devices may be included in or utilize features of an integrated circuit layout. An integrated circuit (IC) layout is also known as an IC layout, IC mask layout, or mask design. The integrated circuit layout is the representation of an integrated circuit in terms of planar geometric shapes which correspond to the patterns of metal, oxide, semiconductor layers, etc., that make up the components of the integrated circuit. Such an integrated circuit layout, including the layout of a semiconductor device, may be stored in a computer readable medium in preparation for fabrication as understood by one skilled in the art.

It will be noted that various microelectronic device fabrication methods may be utilized to fabricate the components/elements discussed herein as understood by one skilled in the art. In semiconductor device fabrication, the various processing steps fall into four general categories: deposition, removal, patterning, and modification of electrical properties.

Deposition is any process that grows, coats, or otherwise transfers a material onto the wafer. Available technologies include physical vapor deposition (PVD), chemical vapor deposition (CVD), electrochemical deposition (ECD), molecular beam epitaxy (MBE) and more recently, atomic layer deposition (ALD) among others.

Removal is any process that removes material from the wafer: examples include etch processes (either wet or dry), and chemical-mechanical planarization (CMP), etc.

Patterning is the shaping or altering of deposited materials, and is generally referred to as lithography. For example, in conventional lithography, the wafer is coated with a chemical called a photoresist; then, a machine called a stepper focuses, aligns, and moves a mask, exposing select portions of the wafer below to short wavelength light; the exposed regions are washed away by a developer solution. After etching or other processing, the remaining photoresist is removed. Patterning also includes electron-beam lithography.

Modification of electrical properties may include doping, such as doping transistor sources and drains, generally by diffusion and/or by ion implantation. These doping processes are followed by furnace annealing or by rapid thermal annealing (RTA). Annealing serves to activate the implanted dopants.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A fluidic sorting device comprising:
   pillars in a nanopillar array on a silicon substrate, the pillars extending vertically straight from the silicon substrate without requiring an oxide formed on the pillars, wherein the pillars in the nanopillar array are designed with a spacing to sort particles of different sizes, and wherein the pillars have an aspect ratio of 100, the pillars comprising a 90 degree angle between a top and side, wherein a mesh is utilized to form the pillars, the mesh being a metal on top of pillars and in direct contact with the silicon substrate;
   at least one or more inlets configured to receive a fluid and the particles to be sorted through the nanopillar array; and
   at least two or more outlets configured to output the particles having been sorted.

2. The fluidic sorting device of claim 1, wherein the metal of the mesh is a selection of noble metals.

3. The fluidic sorting device of claim 1, wherein the metal of the mesh includes Au.

4. The fluidic sorting device of claim 1, wherein the metal of the mesh includes Ag.

5. The fluidic sorting device of claim 1, wherein the metal of the mesh includes Pt.

6. The fluidic sorting device of claim 1, wherein the pillars comprise silicon.

7. A fluidic sorting device comprising:
   pillars in a nanopillar array on a silicon substrate, the pillars extending vertically straight from the silicon substrate without requiring an oxide formed on the pillars, wherein the pillars in the nanopillar array are designed with a spacing to sort particles of different sizes, and wherein the pillars have an aspect ratio of 200, the pillars comprising a 90 degree angle between a top and side, wherein a mesh is utilized to form the pillars, the mesh being a metal on top of pillars and in direct contact with the silicon substrate;
   at least one or more inlets configured to receive a fluid and the particles to be sorted through the nanopillar array; and
   at least two or more outlets configured to output the particles having been sorted.

8. The fluidic sorting device of claim 7, wherein the metal of the mesh is a selection of noble metals.

9. The fluidic sorting device of claim 7, wherein the metal of the mesh includes Au.

10. The fluidic sorting device of claim 7, wherein the metal of the mesh includes Ag.

11. The fluidic sorting device of claim 7, wherein the metal of the mesh includes Pt.

12. The fluidic sorting device of claim 7, wherein the pillars comprise silicon.

13. The fluidic sorting device of claim 7, wherein the pillars are spaced from one another to thereby form the nanopillar array.

* * * * *